US007799057B2

(12) United States Patent
Hudgins et al.

(10) Patent No.: US 7,799,057 B2
(45) Date of Patent: Sep. 21, 2010

(54) TRANSLAMINAR FACET AUGMENTATION AND FLEXIBLE SPINAL STABILIZATION

(75) Inventors: Robert Garryl Hudgins, Burnsville, MN (US); Steven L. Griffith, Eden Prairie, MN (US); Adam Shinbrot, Golden Valley, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 864 days.

(21) Appl. No.: 11/218,846

(22) Filed: Sep. 2, 2005

(65) Prior Publication Data

US 2007/0055236 A1 Mar. 8, 2007

(51) Int. Cl.
*A61B 17/70* (2006.01)
(52) U.S. Cl. ............... 606/247; 606/257; 606/300; 606/320; 606/328
(58) Field of Classification Search ........... 606/247, 606/328, 257, 300, 320; 623/17.11–17.16
See application file for complete search history.

(56) References Cited

U.S. PATENT DOCUMENTS

| | | | | |
|---|---|---|---|---|
| 4,946,202 | A * | 8/1990 | Perricone | 285/153.2 |
| 5,209,751 | A | 5/1993 | Farris et al. | |
| 5,591,166 | A | 1/1997 | Bernhardt et al. | |
| 5,628,740 | A * | 5/1997 | Mullane | 606/307 |
| 5,800,435 | A | 9/1998 | Errico et al. | |
| 6,623,485 | B2 | 9/2003 | Doubler et al. | |
| 6,641,584 | B2 * | 11/2003 | Hashimoto et al. | 606/330 |
| 6,656,184 | B1 * | 12/2003 | White et al. | 606/318 |
| 2005/0055096 | A1 * | 3/2005 | Serhan et al. | 623/17.11 |
| 2005/0113927 | A1 * | 5/2005 | Malek | 623/17.16 |
| 2005/0131405 | A1 * | 6/2005 | Molz et al. | 606/61 |
| 2005/0177240 | A1 * | 8/2005 | Blain | 623/17.15 |
| 2006/0036323 | A1 * | 2/2006 | Carl et al. | 623/17.11 |
| 2006/0190081 | A1 * | 8/2006 | Kraus et al. | 623/17.11 |

(Continued)

FOREIGN PATENT DOCUMENTS

NL 7610576 3/1978

OTHER PUBLICATIONS

"cord." The Online Plain Text English Dictionary [online], [retrieved on Feb. 9, 2009]. Retrieved from the Internet <URL: http://www.onelook.com/?other=web1913&w=Cord>.*

(Continued)

*Primary Examiner*—Eduardo C Robert
*Assistant Examiner*—Ellen C Hammond
(74) *Attorney, Agent, or Firm*—Crompton, Seager & Tufte, LLC

(57) ABSTRACT

The present invention is an apparatus and method for stabilizing the facet joints of the spine. One aspect of the present invention is the stabilization of the facet joint by insertion of a facet implant through two opposing facet surfaces. The facet joint is not fixedly frozen by insertion of the screw, but instead the facet surfaces are flexibly and movably anchored to preserve movement because the screw or anchor includes a flexible intermediate portion which is positioned between the facet surfaces. The facet implant may be in the form of a screw or other anchor with the intermediate portion in the form of a polyaxial head, a cord, a spring, etc. The facet implant may furthermore be used in conjunction with a facet spacer that is placed between the first and second facet.

9 Claims, 16 Drawing Sheets

U.S. PATENT DOCUMENTS

2006/0235414 A1* 10/2006 Lim et al. .................. 606/73
2009/0125066 A1* 5/2009 Kraus et al. ................ 606/279

OTHER PUBLICATIONS

Humke et al., "Translaminar Screw Fixation of the Lumbar and Lumbosacral Spine (A 5-Year Follow-Up)", *Spine*, May 15, 1998, pp. 1180-1184, vol. 23, No. 10, 1998 Lippincott-Raven Publishers.

*Orthopedic Spine Surgery: Cervical Spine*, Regional Orthopedic Center, Poudre Valley Hospital, Fort Collins, Colorado.

Lu et al., "Translaminar Facet Screw Placement: An Anatomic Study", *American Journal of Orthopedics*, Aug. 1998, pp. 550-555, vol. 27, No. 8, Department of Orthopaedic Surgery, Medical College of Toledo, Ohio.

* cited by examiner

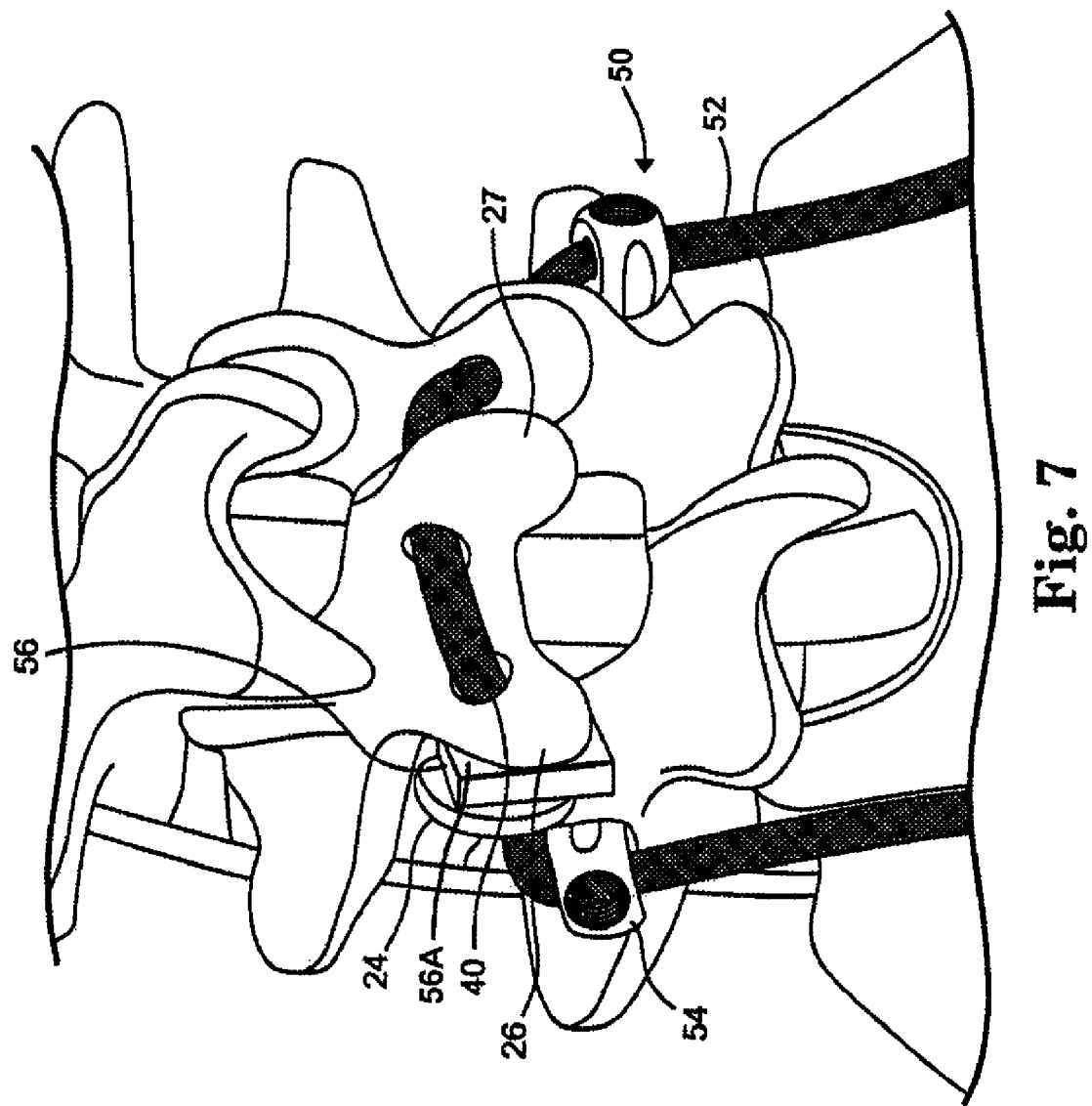

TRANSLAMINAR FACET AUGMENTATION AND FLEXIBLE SPINAL STABILIZATION

TECHNICAL FIELD

The present invention is related to spinal stabilization devices. More particularly, the present invention relates to an apparatus and method for addressing back pain in the vertebrae while providing joint stabilization.

BACKGROUND

The spinal column is a highly complex system of bones and connective tissues that provides support for the body and protects the delicate spinal cord and nerves. The spinal column includes a series of vertebrae stacked one on top of the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal cord and nerves is located behind the vertebral bodies.

The bones and connective tissue of an adult human spinal column consists of more than 20 discrete bones coupled sequentially to one another by a tri-joint complex which consist of an anterior disc and two posterior facet joints. The anterior discs of adjacent bones are cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine up to the base of the skull, includes the first 7 vertebrae. The intermediate 12 bones are the thoracic vertebrae, and connect to the lower spine comprising the 5 lumbar vertebrae. The base of the spine is the sacral bone (including the coccyx). The component bones of the cervical spine are generally smaller than those of the thoracic and lumbar spine. In spite of these complexities, the spine is a highly flexible structure, capable of a high degree of curvature and twist in nearly every direction.

A few parts of the spine include the pedicle, the laminar arch, the facet, the spinous process, the transverse process, the vertical canal and the vertebral body. The vertebral body is the cylinder-shaped weight bearing-structure of the vertebra. The lamina are flat plates on the outer wall of the vertebral canal, which is formed between the vertebral body and the lamina and occupied by the spinal cord. The pedicle connects the lamina with the vertebral body. The spinous process protrudes from the back of the vertebra such that muscles and ligaments can attach thereto. Finally, the transverse process sticks out the sides of each vertebra and are another place where muscles and ligaments can attach to the spine.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain, as well as diminished nerve function. These spinal disorders, pathologies, and injuries limit the spine's range of motion, or threaten the critical elements of the nervous system housed within the spinal column.

One of the most common surgical interventions today is arthrodesis, or spine fusion, of one or more motion segments. Clinical success varies considerably depending upon technique and indications. Consideration also must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused segments. Also, the fusion device, whether artificial or biological, may migrate out of the fusion site.

A variety of devices and systems have been disclosed in the art that achieve spine fusion and immobilization by implanting artificial assemblies in or on the spinal column. These assemblies may be classified as anterior, posterior, or lateral implants. As the classifications suggest, anterior assemblies are coupled to the anterior portion of the spine, which is the sequence of vertebral bodies. Anterior stabilization methods include full or partial disc replacements with rigidly shaped spacers that are appropriately sized for the disc space. Posterior implants generally comprise pairs of rods that are aligned along the axis to be immobilized. The implants are attached to the spinal column by hooks coupled to the lamina or to the transverse processes or by screws inserted through the pedicles.

Other methods include flexible spinal stabilization methods that do not result in complete spinal fusion. Posterior stabilization methods may include spinal immobilization utilizing a pedicle screw and wire system. Another flexible posterior stabilization method includes the Dynesys™ system. The Dynesys™ system allows spinal segments to be placed back into position and fixed there while restricting, but not completely preventing, movement. Other systems are for the focused stabilization of particular areas of the vertebrae, such as the pedicles or facets.

SUMMARY

The present invention relates to a spinal stabilization system that focuses on stabilizing an opposing pair of facet surfaces by using an anchor, screw, or post with a flexible portion. The system maintains joint mobility while still providing stabilization. The flexible mechanism may be a screw or other anchoring system with a spring, cable, cord, hinge, or other flexible section, including combinations thereof, which may effectively bridge the two opposing facet surfaces to provide increased stability.

One embodiment of the present invention includes a facet implant for stabilizing a first and a second adjacent vertebrae including a first implant member positionable and attachable through a facet of the first vertebra, a second implant member positionable and attachable through a facet of the second vertebra, wherein the first vertebra facet opposes the second vertebra facet, and an intermediate implant element between the first and second implant members positionable between the first and second vertebra facets that controls the relative movement between the first and second vertebrae.

The present invention is also a system for stabilizing an opposing pair of facet surfaces including a facet implant for insertion between an opposing pair of facet surfaces, the facet implant including an articulating surface and at least one fixation tab, the facet implant providing spacing and support to the opposing facet surfaces, a cord for insertion through the opposing pair of facet surfaces and the facet implant, and at least one bone anchor for anchoring the cord to the spine.

The present invention also includes a method of stabilizing a facet joint including drilling a receiving hole through an opposing pair of facet surfaces and inserting a facet implant into the receiving hole such that it extends through the opposing surfaces, the facet implant including an intermediate element positioned between the opposing facet surfaces for controlling the relative movement of the pair of facet surfaces.

The present invention is furthermore a method for stabilizing a facet joint including securing together two opposing facet surfaces of a facet joint with a screw, the screw including a distal element, a proximal element, and an intermediate portion, the intermediate portion positionable and attachable between the two opposing facet surfaces and providing improved structural stability to the facet joint but to also allow for movement of the facet surfaces in relation to one another, the screw extending through a portion of the lamina and the transverse process.

Yet another embodiment is an apparatus for stabilizing a first and a second adjacent vertebra including a screw including a proximal element, a distal element, and an intermediate portion, the proximal element and the distal element including external screw threads and connected by the intermediate portion such that the proximal element and the distal element may move relative to each other, the screw placed through a lamina of a spine, through a pair of opposing facet surfaces of a facet joint, and into the transverse process, the intermediate portion positioned between the opposing pair of facet surfaces of the facet joint.

While multiple embodiments are disclosed, still other embodiments of the present invention will become apparent to those skilled in the art from the following detailed description that shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention teaches an apparatus and method for stabilizing a facet joint 18 of the spine. One aspect of the present invention is the insertion of screws through the laminar arch of the vertebral bone and through two opposing facet surfaces 24 and 26 to stabilize the facet joint 18. The facet joint 18 is not fixedly frozen by insertion of the screw, but instead the facet joint 18 is flexibly and movably anchored because the screw or anchor includes a flexible portion positioned between the facet surfaces 24 and 26. The present invention helps to stabilize flexion, extension, rotation, and lateral bending. Stabilizing the spine includes limiting the movement of the spine a desired amount but preferably not including complete immobilization. In general, one goal of the present invention may be to stabilize the spine but to retain the capability of the spine for many degrees of movement.

Figure 1:
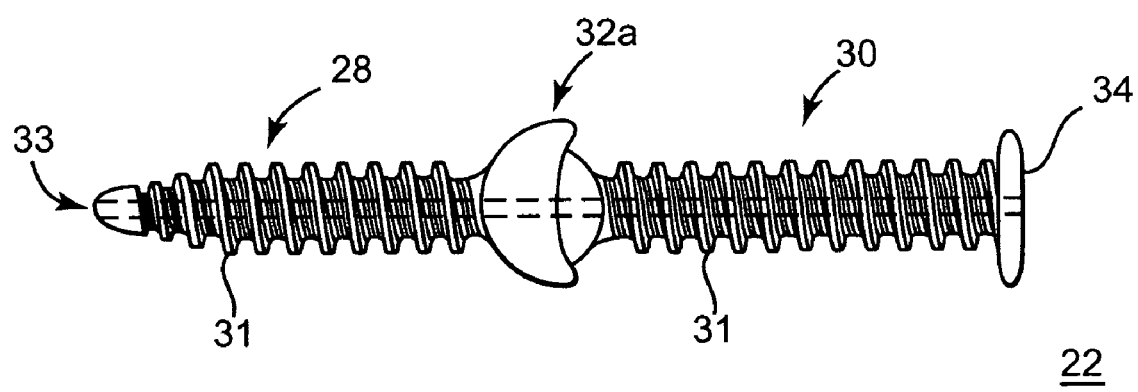
FIG. 1 illustrates a facet implant of the present invention including two cannulated screw shafts connected by a polyaxial head.

FIG. 1 illustrates one embodiment. A facet implant 22 for placement through two opposing facet surfaces 24 and 26 of the selected facet joint 18 includes a distal element 28, a proximal element 30, an intermediate portion 32a and a head 34. The intermediate portion 32a connects the distal element 28 and the proximal element 30 (which may also be referenced as the lower and upper ends or distal body and proximal body, respectively) and allows for relative motion or movement of the distal element 28 relative to the proximal element 30. The distal element 28 and the proximal element 30 are not necessarily the same length. The facet implant 22 may be placed so that the intermediate portion 32a is disposed between the facet surfaces 24 and 26. The screw 22 may also be affixed through a portion of the lamina 27 and extend a desired distance into the transverse process 29. The head 34 is affixed to a top portion of the proximal element 30 and includes a fixation interface 36. The fixation interface 36 may be any kind of screw, such as flat, phillips, hex, or any standard or custom interface means. The facet implant 22 may be any kind of facet implant 22 including a screw, bolt, shaft, bar, dowel, fastener, peg, pin, pipe, rivet, rod, spike, stake, and staple. The facet implant 22 may also be other mechanical bodies for securing the facet surfaces 24 and 26, such as a post, but the term "screw 22" will be used herein to generally represent the use of any securing means.

The distal element 28 and proximal element 30 of screw 22 both include external threads 31 such that screw 22 may be secured to the bone of the spine. Any type of thread variation known in the art may be used. The proximal element 30 and the distal element 28 may be made of any material known in the art to be useful for making biomedical screws, such as, but not limited to, stainless steel, titanium, and other alloys. Also incorporated into the screws 22 may be various biomedical plastics, polymers, elastomers, carbon fibers, Dacron™, polytetrafluorethylene, etc.

Figure 2:
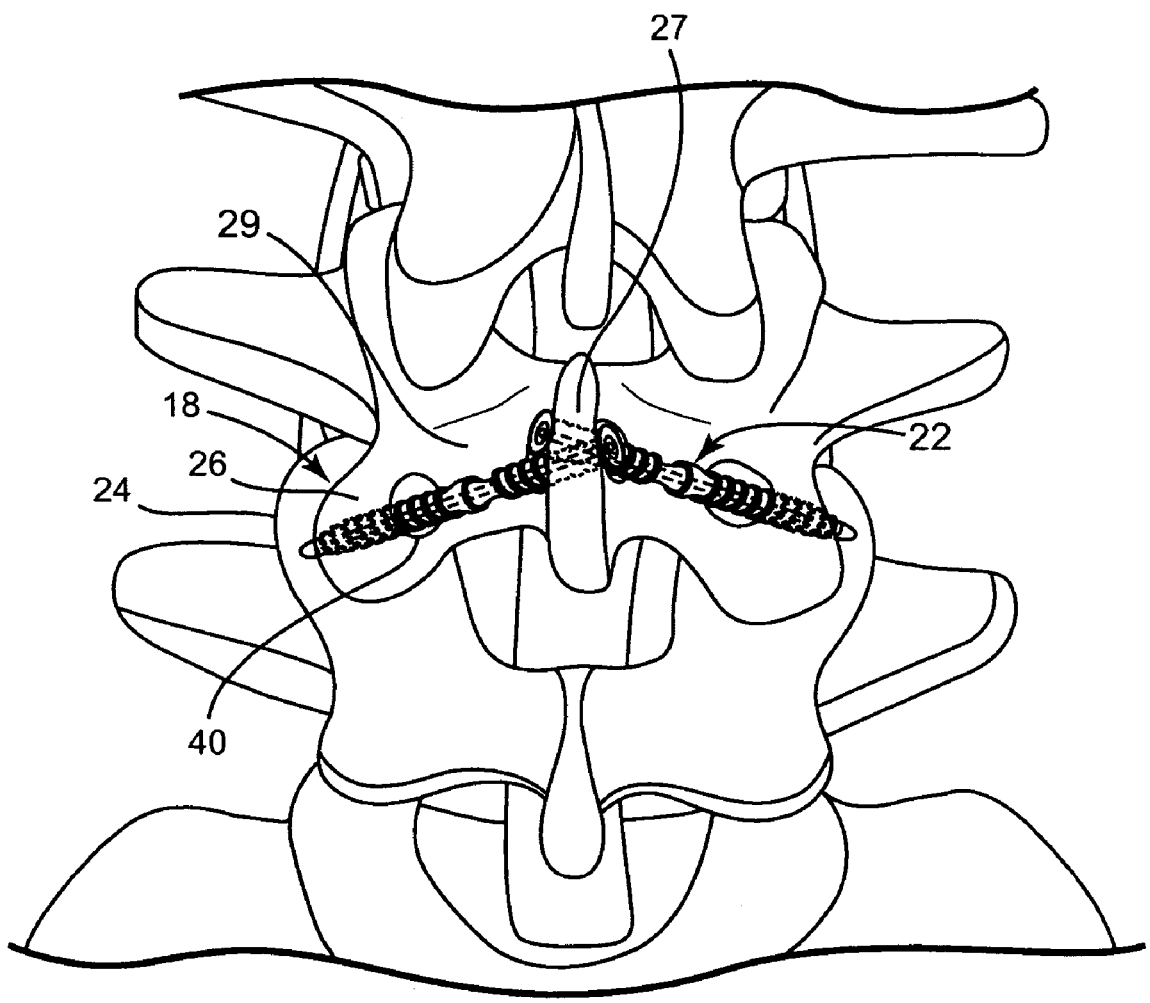
FIG. 2 illustrates the facet implant of FIG. 1 inserted into the spine.
Figure 3:
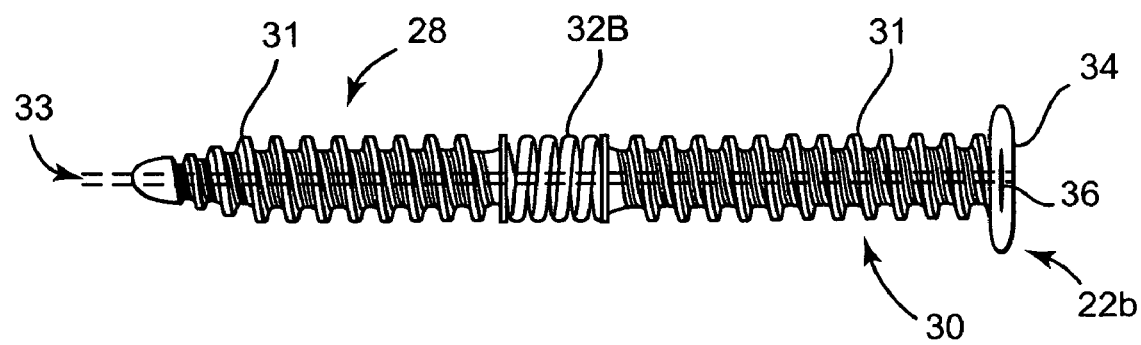
FIG. 3 illustrates a facet implant device of the present invention including two cannulated screw bodies connected by a coiled spring.
Figure 4:
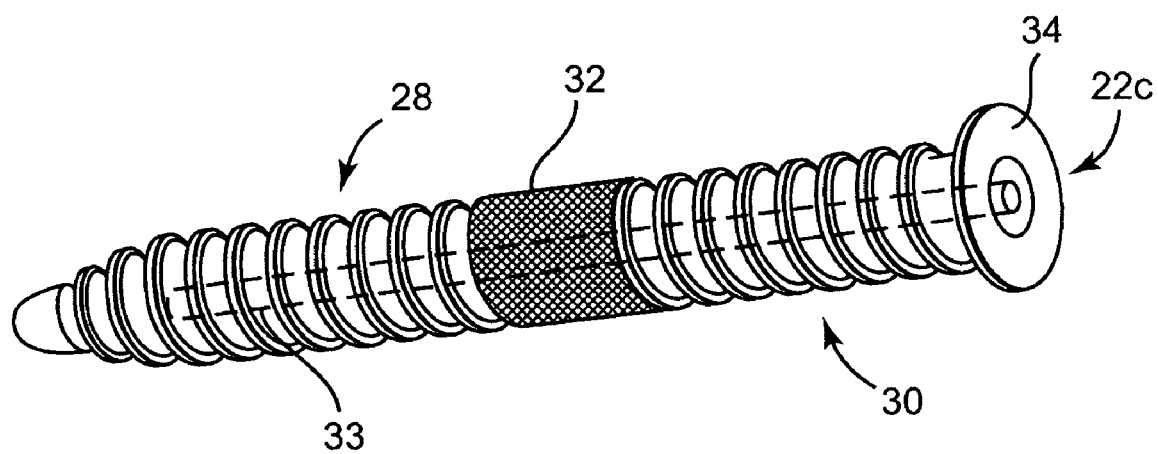
FIG. 4 illustrates a facet implant device of the present invention including two screw bodies connected by a cord.

The intermediate portion 32a provides means for flexibly connecting the distal element 28 to the proximal element 30. Because the entire screw 22 is not a solid shaft, screw 22 allows for stabilized enhancement of the opposing facet 24 and 26 without complete immobilization. The intermediate portion 32a may include a variety of flexible components and may be an articulating, bendable or flexible member, joint, joint member, or articulating member. FIGS. 1-2 illustrate the intermediate portion 32a as a polyaxial joint. The polyaxial joint may be adjusted to require a greater or lesser amount of force to move or rotate depending on the stabilization desired. In this manner, the degree of stabilization of the facet joint may be selectively adjusted in regards to the amount of stiffness, flexibility, extensibility, compressibility, looseness, etc. the screw 22 imparts upon the facet surfaces 24 and 26. In one alternative embodiment shown in FIG. 3 the facet implant 22b includes an intermediate portion 32b that is a spring. In another alternative embodiment shown in FIG. 4, the facet implant 22c includes an intermediate portion 32c that is a cord. In further embodiments any number of flexible, bendable, loose, or stiff constructs, including, but not limited to, a coiled spring, cord, wire, chain, band, ball, ball and socket, U-joint, other joints, or a bendable element such as a plastic or elastomer. In addition, other connecting systems known in the art may also be incorporated into the present invention.

Figure 8:
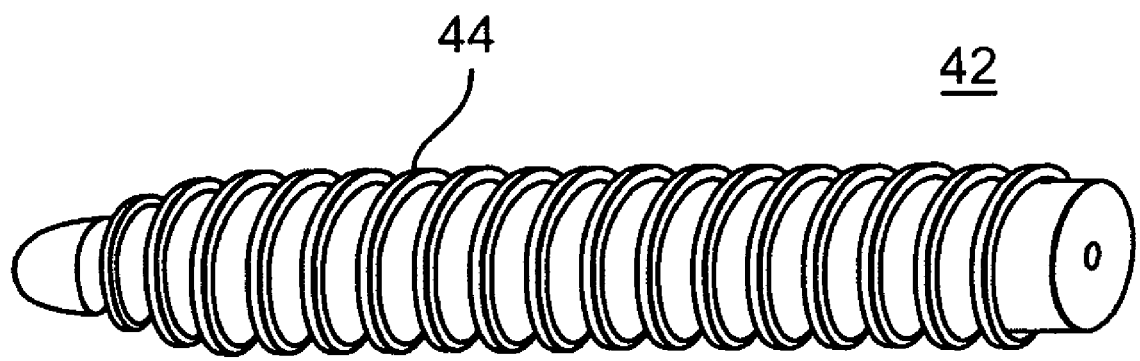
FIG. 8 illustrates an introducer that fits in a lumen or channel of the facet implant of the present invention.

In one embodiment, the screw 22 is a cannulated screw. A cannulated screw 22 is a screw that has a hollow bore 33 through at least a portion of the screw shaft. A cannulated screw need not have a head. The hollow bore 33 of the screw 22 may include or receive an introducer 42 as illustrated in FIG. 8. The introducer 42 is a removable member that extends through the hollow bore 33 of the distal element 28, proximal element 30, and intermediate portion 32a of the cannulated screw 22. The introducer 42 may include external left hand threads 44 that engage with corresponding internal threads (not shown) on the inside of screw 22. The introducer 42 provides structural stability to the intermediate portion 32a to allow for insertion. The introducer 42 also goes through the intermediate portion 32a (the cord, polyaxial head, spring, etc.) to stop the intermediate portion 32a from binding, bending, or otherwise moving relative to the distal element 28 and proximal element 30 during screw 22 placement. The left-hand threads 44 allow the introducer 42 to engage the screw 22 during insertion and to be disengaged from the screw 22 thereafter.

To insert a screw 22, a small incision is first made and then the tissue is retracted. Beginning at a point superior to the spinous process on the contralateral side of the facet joint that is to be stabilized, a drill is used to drill a hole 40 through opposing facet surfaces 24 and 26. The hole 40 may be drilled through a portion of the lamina 27 and into the transverse process 29 or the underlying pedicle. The hole 40 may be created at a desired depth and at a desired angle. If desired, the hole 40 may be extended into the transverse process 29 or the underlying pedicle. As may be appreciated, some amount of ablation of the facet surfaces 24 and 26 and the connective tissue between facet surfaces 24 and 26 may be required or desired depending on the size and shape of the intermediate portion 32a. Moreover, various distal elements 28 and proximal elements 30 of different sizes and lengths may be attached by a range of intermediate portions 32 of various sizes to customize the screws 22 for each patient. In further embodiments, the insertion of the screw 22 may be accomplished through the use of a cannula and may also include the use of minimally invasive techniques. Minimally invasive techniques may include the use of a guidewire or other instruments known to those in the art.

The drill 38 may then be removed from the hole 40. A measuring device may be inserted into the hole 40 to measure the depth of the hole 40 and the location of the facet surfaces 24 and 26, such that the proper length screw 22 may be selected to better insure that the intermediate portion 32a is properly placed between facet surfaces 24 and 26. Furthermore, a guide wire may be inserted into the hole 40 and used to guide the screw 22 into the proper position. The hole and/or the screw 22 may be inserted to a depth so that the intermediate portion 32a may be positioned between facet surfaces 24 and 26. The screw 22 is inserted by utilizing an appropriate screwdriver for head 34 and fixation interface 36. The screw 22 may be countersunk if desired. A surgical guideframe could be utilized to aid with implantation of the screw 22, though may not be necessary. The method may also include tapping the drilled hole to accommodate the screw's geometry. Alternatively, the screw's threads may be self drilling or self tapping.

As may be appreciated, the flexibility and support provided by the intermediate portion 32a may be selected depending on the desired clinical outcome. Depending on how much the movement of the facet surfaces 24 and 26 needs to be restricted, the intermediate portion 32a may be made more or less stiff. The type of intermediate portion 32a may contribute to the amount of "stiffness" provided by screw 22 to the facet joint 18. Further, the type of intermediate portion 32a may determine the permitted movement between the opposing facets 24 and 26, e.g., a u-joint would allow for rotating movement around one axis and a polyaxial joint would allow for rotating around a plurality of axes.

After the screw 22 has been inserted to the proper depth, the introducer 42 may be then removed from the screw 22. The head 34 of the screw 22 may be sealed using a set screw or plug, or, alternatively, left open. A screw 22 that was not a cannulated screw may also be used. Such a screw 22 may include a polyaxial head that may be locked during insertion and then unlocked for free movement after insertion.

Figure 9:
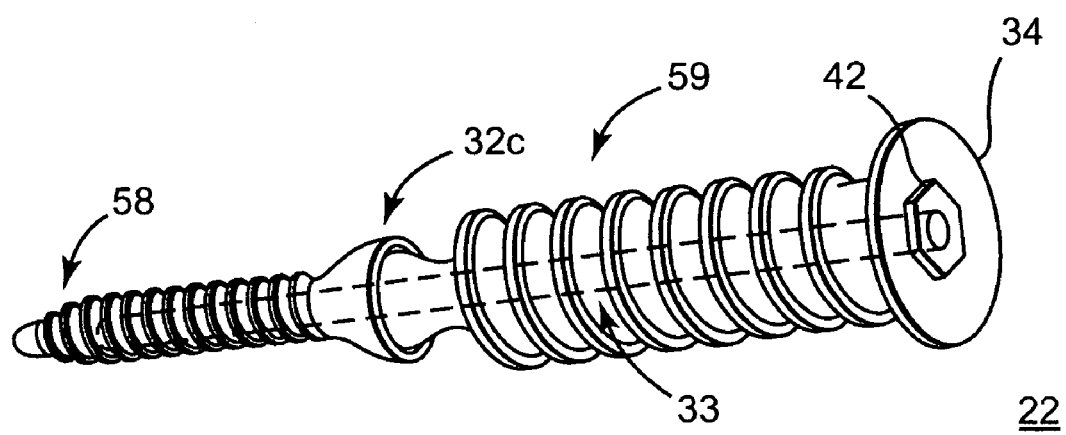
FIG. 9 illustrates an alternative embodiment of the facet implant of FIG. 1.

In another alternative embodiment illustrated in FIG. 9, the facet implant 22d may include a distal element 58 with a smaller diameter than the intermediate portion 32d and the proximal element 59. Moreover, the proximal element 59 may have a diameter equal to or greater than that of the intermediate portion 32c. The smaller diameter of the distal element 58 may engage the base of the transverse process 29 and the larger diameter of the proximal element 59 may engage the penetration point of the lamina 27. Thus, the hole 40 created in the lamina 27 may be large enough to allow passage of the intermediate portion 32c, but the distal element 58 may be small enough to reduce the risk of fracturing the facet surfaces 24 and 26 during placement.

Figure 10:
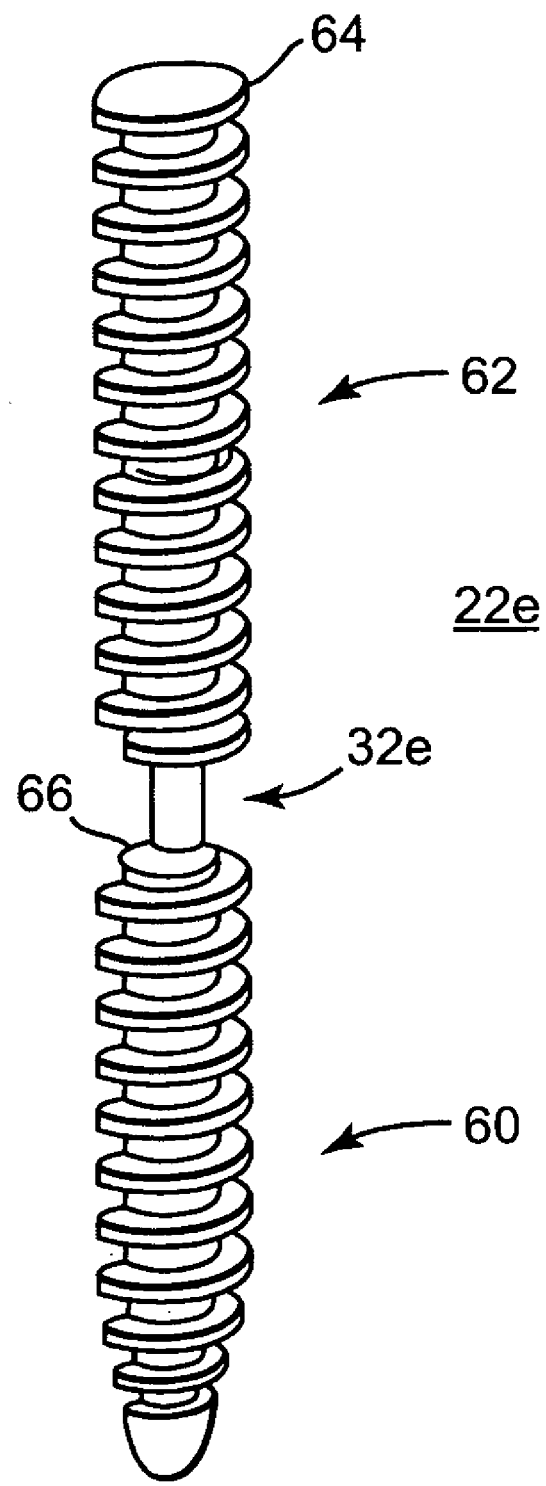
FIG. 10 illustrates another alternative embodiment of the facet implant of FIG. 1.
Figure 11:
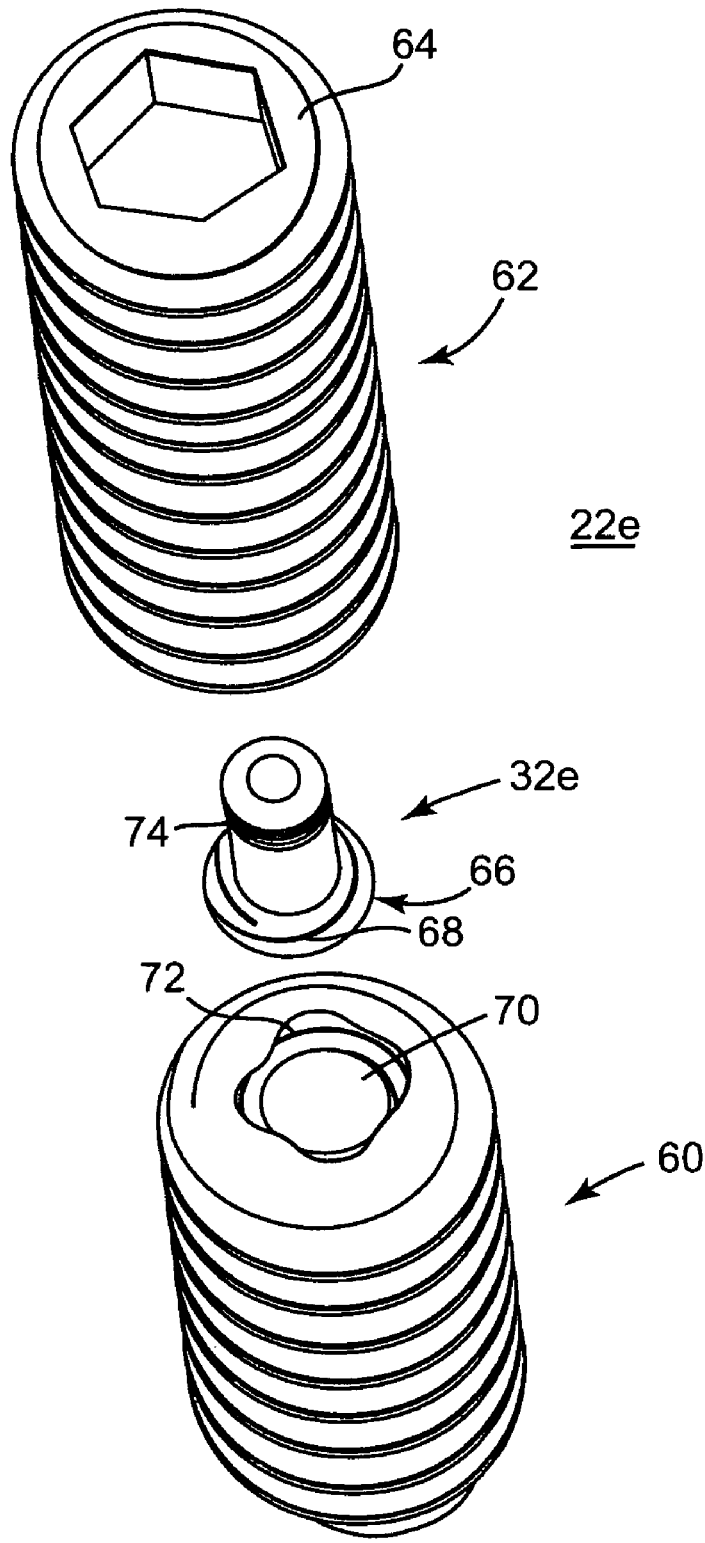
FIG. 11 illustrates a top view of the facet implant of FIG. 10.

As illustrated in FIGS. 10-11, another alternative embodiment of the present invention facet implant 22e with a distal element 60, a proximal element 62, an intermediate portion 32e and a head 64. The intermediate portion 32e connects the distal element 60 and the proximal element 62. The intermediate portion 32e may be affixed to the proximal element 62 and include a ball 66 with screw threads 68 disposed on an outside portion thereof. The distal element 60 may further include a shaped cavity 70 for receiving the ball 66. The shaped cavity 70 may include screw threads 72 on a portion thereof for engaging screw threads 68. The intermediate portion 32e may also include screw threads 74 on a proximal end for engaging screw threads (not shown) on an interior portion of the proximal element 62.

The proximal element 62 and the distal element 60 of this alternative embodiment facet implant 22e may be placed separately. The distal element 60 may be inserted into a pre-drilled hole. The distal element may be a self-centering screw, or, in further embodiments, may be a self-tapping screw that does not require a pre-drilled hole. For insertion, the distal element 60 may include an interface for an insertion device at the bottom of cavity 70. The distal element 60 may be inserted through the lamina 27 and into the desired position in the transverse process 29. The proximal element 62, with the intermediate portion 32e first attached thereto, may then be placed through the lamina 27 to mate with the distal element 60. In other embodiments, the insertion device may interface with the distal element 60 in any manner known to those of skill in the art. In addition, the distal element 60 and proximal element 62 may be laterally offset or may include axes that are offset.

The screw threads 68 of the ball 66 engage the screw threads 72. In the present embodiment, the engagement of screw threads 68 and 72 may help to draw the proximal portion 62 and the distal portion 60 of the facet implant 22e and into the desired position and/or alignment. Once the proximal portion 62 and distal portion 60 are in the proper alignment and position, the proximal portion 62 may be screwed a predetermined additional amount to move the ball 66 into a desired position in cavity 70. By continuing to screw the proximal portion 62 through the bone the screw threads 68 of the ball 66 are moved past the zone occupied by screw threads 72. The ball 66 is then pushed into and disposed in cavity 70 by continued movement of the proximal element 62.

With the ball 66 disposed in cavity 70 the proximal element 62 and the distal element 60 may be in a desired multiaxial relationship. The screw threads 68 and 72 may prevent the ball 66 from backing out of the cavity 70 and thereby insure that the proximal element 62 and the distal element 60 remain affixed. As may be appreciated, the ball 66 can be positioned into the cavity 70 in a number of ways, including, such as, the ball 66 being compressible such that it fits through the cavity. Further, the screw threads 68 and 72 can be arranged such that no dimensional change is required during insertion.

Figure 12:
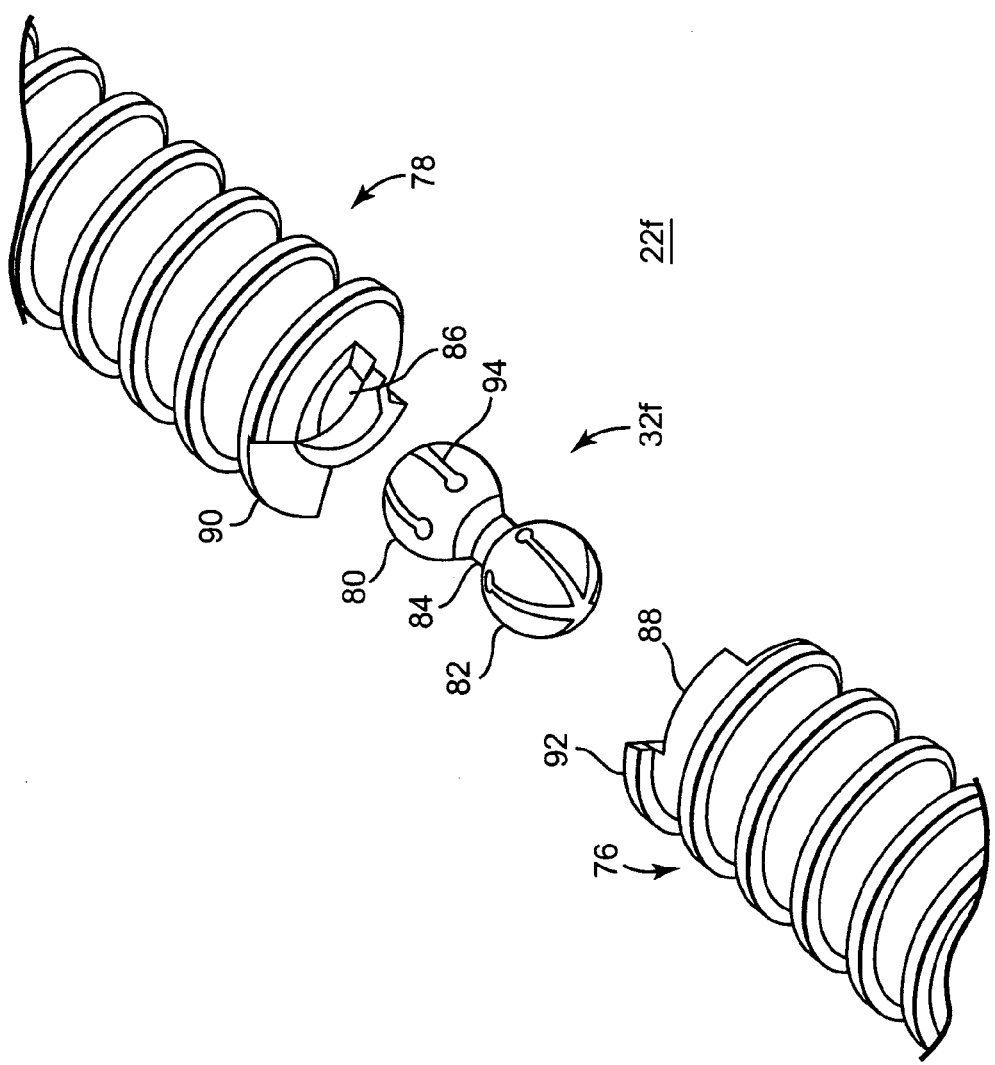
FIG. 12. illustrates a perspective view of another embodiment of the facet implant of FIG. 1.
Figure 13:
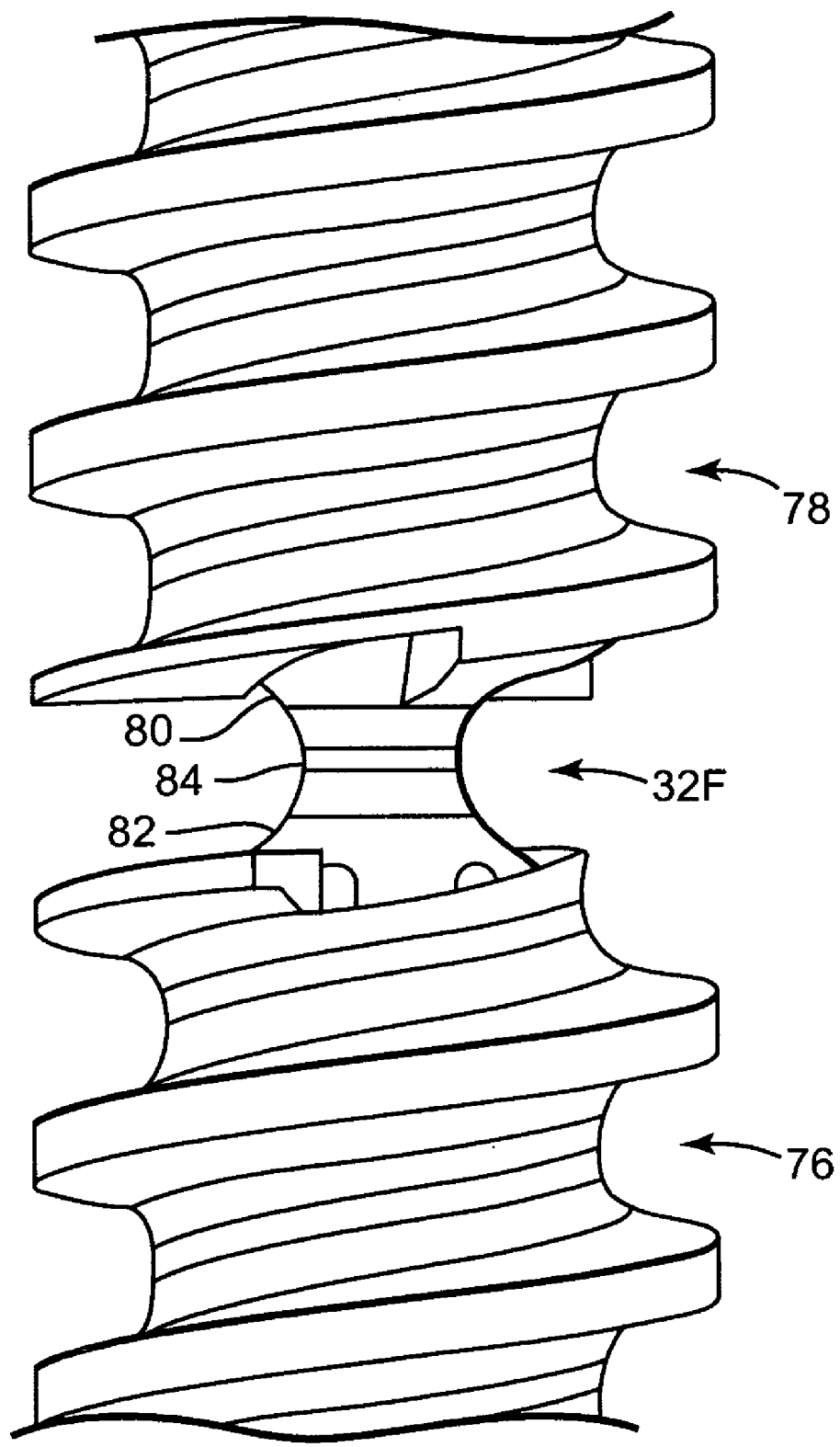
FIG. 13 illustrates a side view of the facet implant of FIG. 12

FIGS. 12-13 show another embodiment of the present invention. In this embodiment, a facet implant 22f includes a distal element 76, a proximal element 78, and an intermediate portion 32f. The distal element 76 and the proximal element 78 are portions of a screw shaft with screw threads. The intermediate portion 32f further includes a double ball configuration with a first ball 80 and a second ball 82 connected by a shaft 84. The first and second balls 80, 82 may fit into a corresponding cavity 86, 88 in the distal element 76 and the proximal element 78. The interaction of the first and second ball 80, 82 and the corresponding cavity 86, 88 act like a ball and socket and create a multiaxial joint. The facet implant 22e further includes complimentary interfaces 92 and 90 on the distal element 76 and proximal element 78, respectively. The first and second balls 80, 82 may furthermore include a number of slits 94. The slits 94 allow the first and second balls 80, 82 to deform such that the first and second balls 80, and 82 can be inserted into the corresponding cavity 86, 88 by snap fitting.

Figure 14:
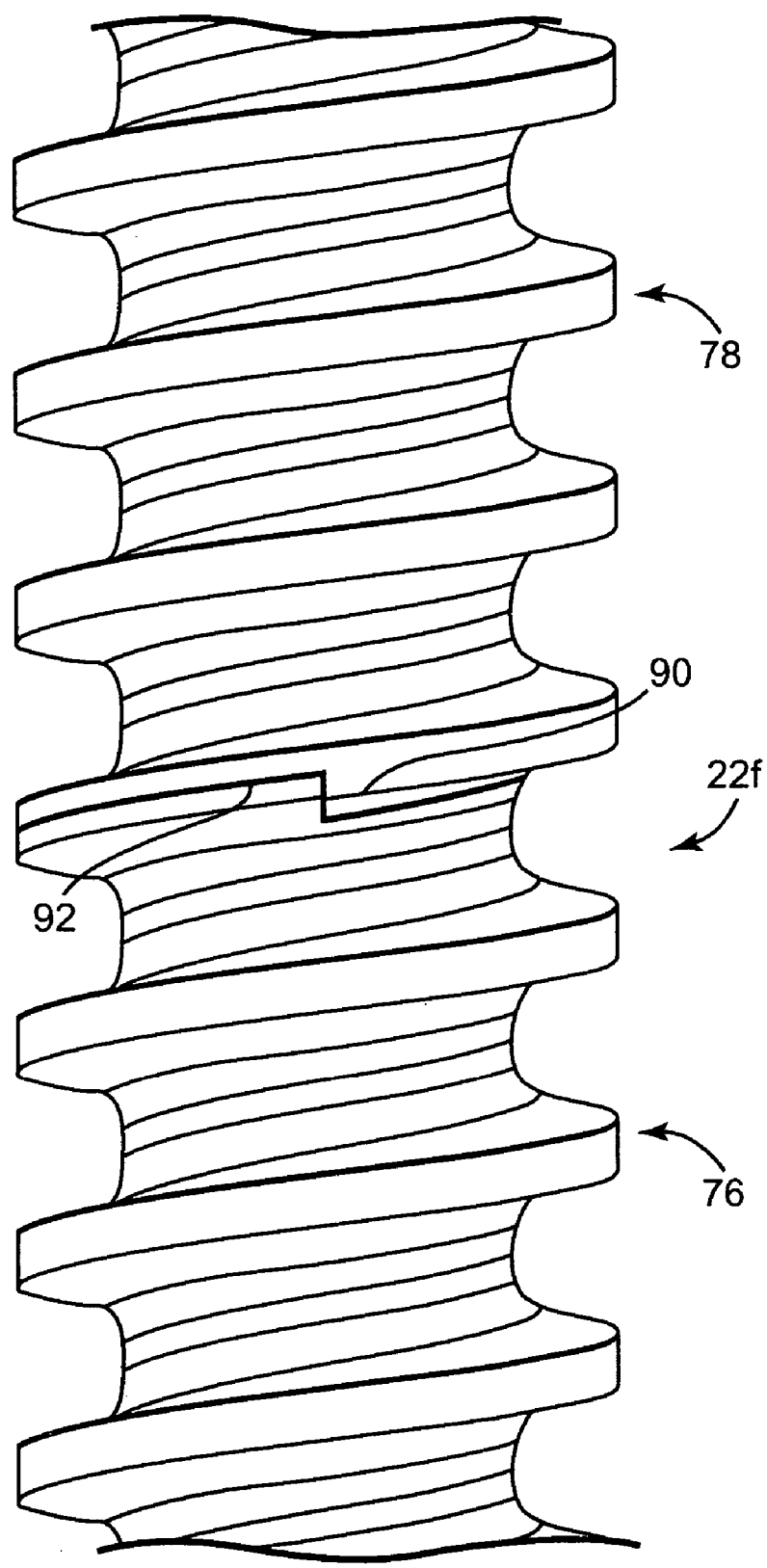
FIG. 14 illustrates another side view of the facet implant of FIG. 12.
Figure 15:
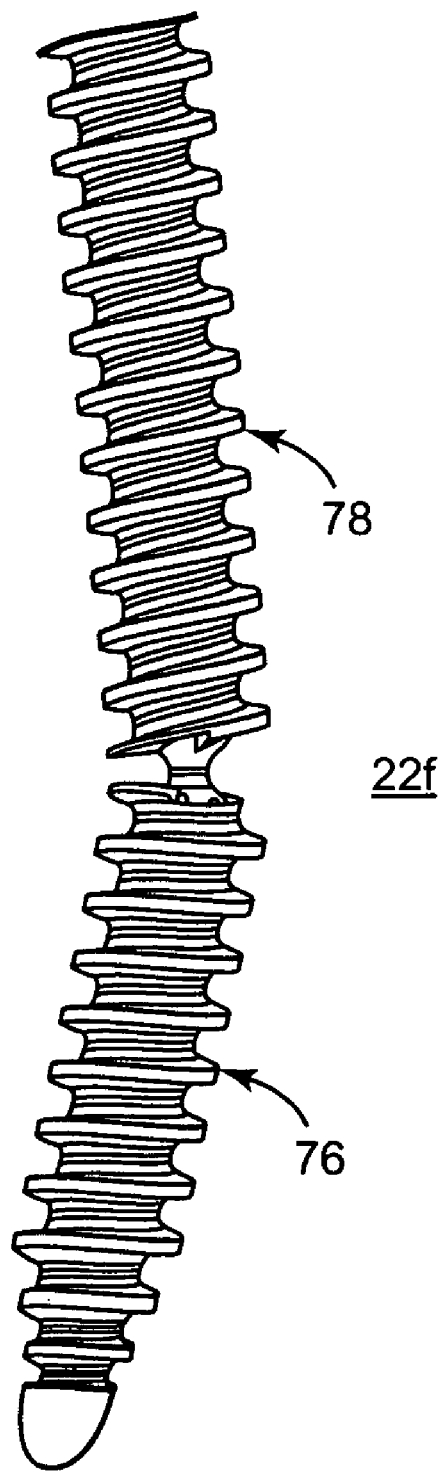
FIG. 15 illustrates yet another side view of the facet implant of FIG. 12.

As shown in FIG. 14, during insertion the complimentary interfaces 92 and 90 are brought into contact with each other and engage. When the complimentary interfaces 92 and 90 engage, rotation of the proximal element 78 can be translated to the distal element 76. In this manner the facet implant 22f can be screwed into the desired location without needing an introducer or other element to temporarily join the proximal element 78 to the distal element 76. As in previous embodiments, the facet implant 22f can be inserted a number of ways, such as using a pre-drilled hole, a self tapping screw, etc. Furthermore, each cavity 86, 88, is sized to receive the first and second ball 80, 82 therein when the complimentary interfaces 92 and 90 are brought into contact. The intermediate element 32f fits in the two cavities 86, 88 during insertion. The complimentary interfaces 92 and 90 can be any type of complimentary pair of sprags, pawls, tooths, gears, etc. Once the distal element 76 is inserted to the desired depth, the proximal element 78 may be unscrewed a desired number of rotations. The reverse rotation does not engage the complimentary interfaces 92 and 90 and so the distal member 76 stays in place. As illustrated in FIG. 15, the facet implant 22f now acts as a multiaxial joint.

Figure 5:
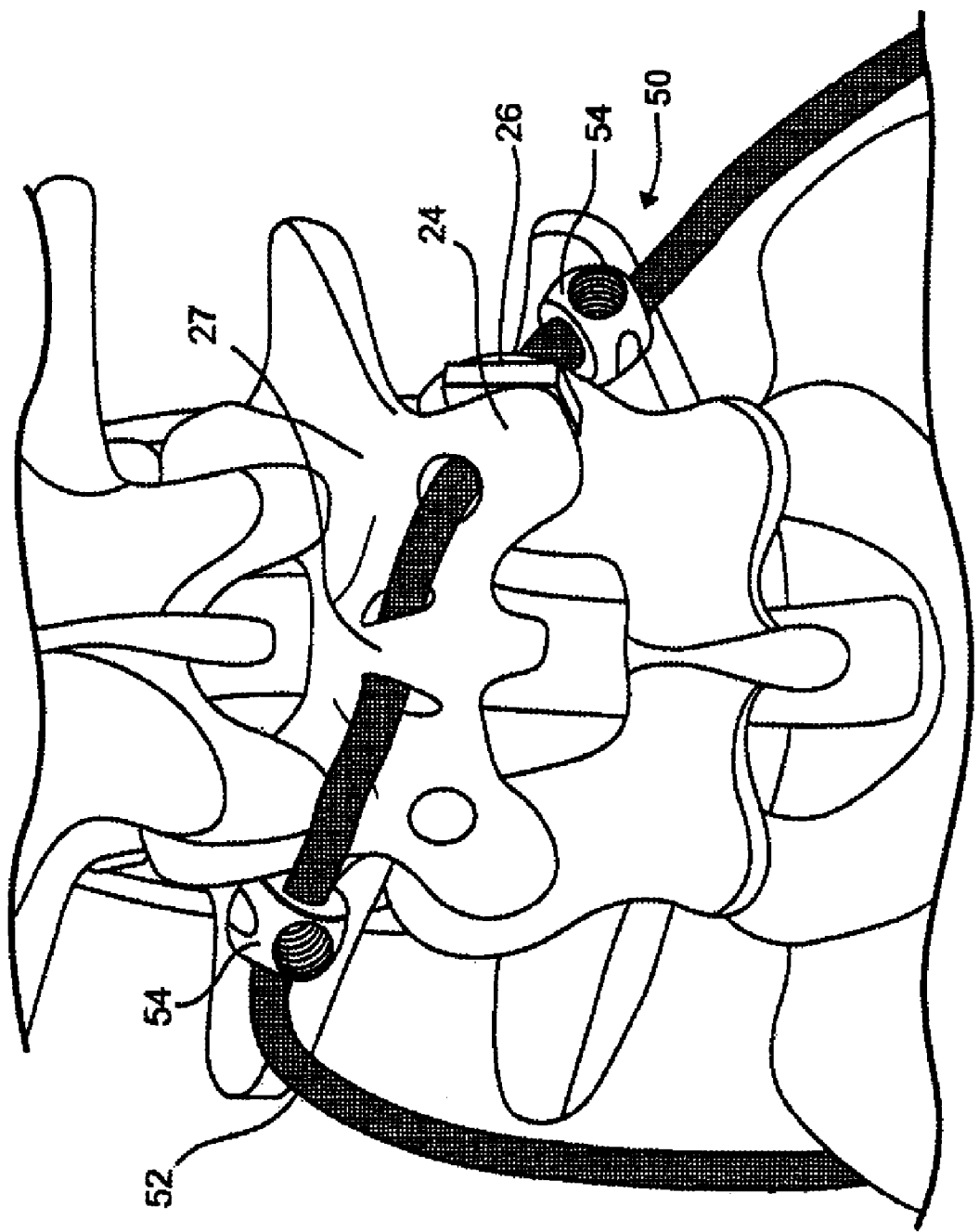
FIG. 5 illustrates an alternative embodiment of the present invention including a cord placed through the opposing surfaces of one facet, through the lamina in a transverse direction, and secured to the spine.
Figure 6:
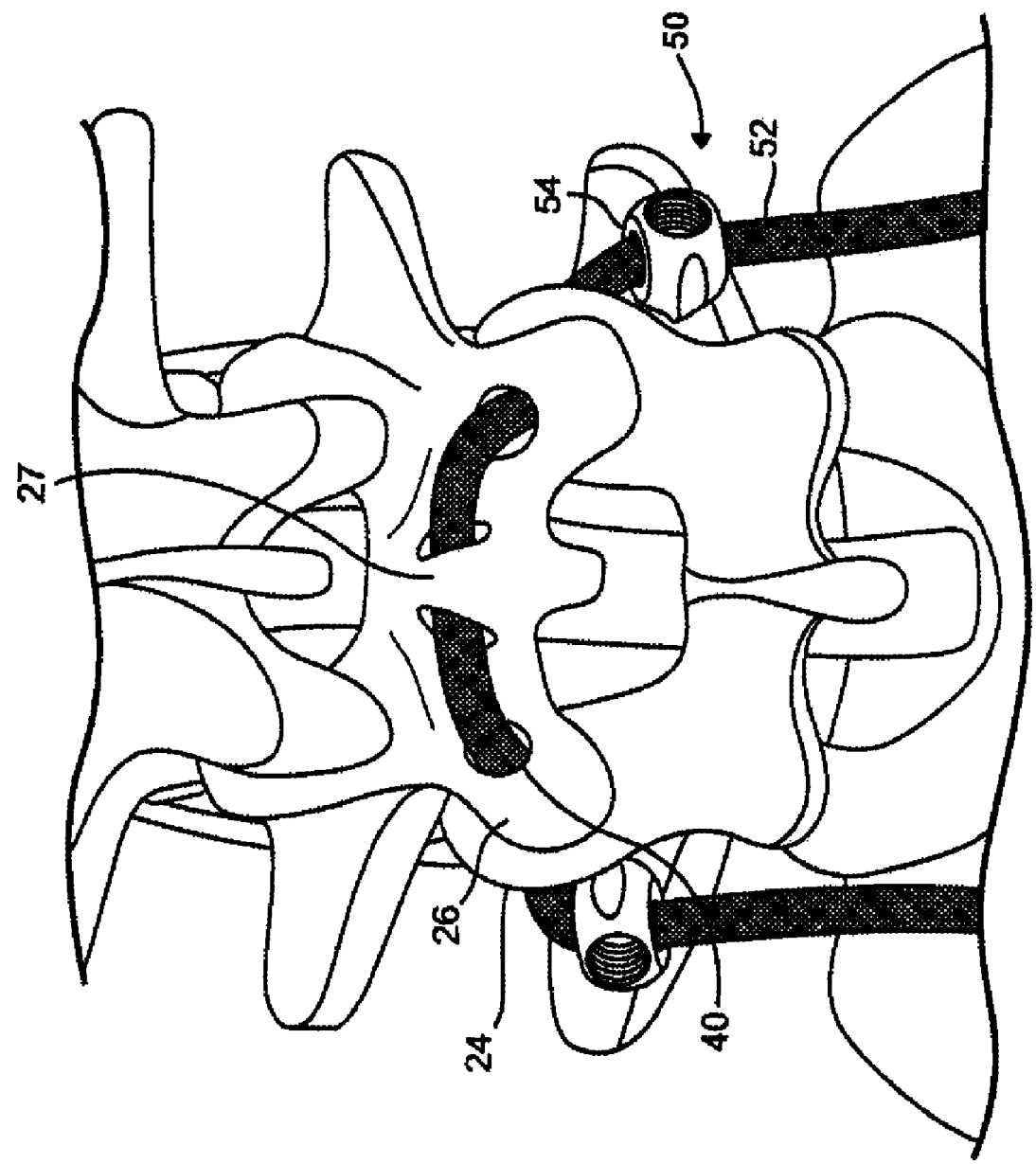
FIG. 6 illustrates an alternative embodiment of the present invention including a cord placed through the opposing facet surfaces of two facets and the lamina and secured to the spine.

In another alternative embodiment illustrated in FIGS. 5-7, a spinal stabilization system 50 may include a cord 52 and at least one bone fixation member 54. The cord 52 may be inserted through the opposing facet surfaces 24 and 26 and the lamina 27. The cord 52 may be anchored utilizing bone fixation member 54. Such a bone fixation member 54 may be a screw like the one utilized in the prior art Dynesys™ system.

The cord 52 may be passed through the opposing facet surfaces 24 and 26 and through the lamina 27, and possibly a portion of the spinous process, and then anchored by the bone fixation member 54. The tension placed on cord 52 may be selectively adjusted to result in the desired stabilization of the spine. The modulus of elasticity of the cord may be another useful variable. The path of cord 52 may be selectively adjusted to provide the desired support to the desired portion of the spine.

Figure 7A:
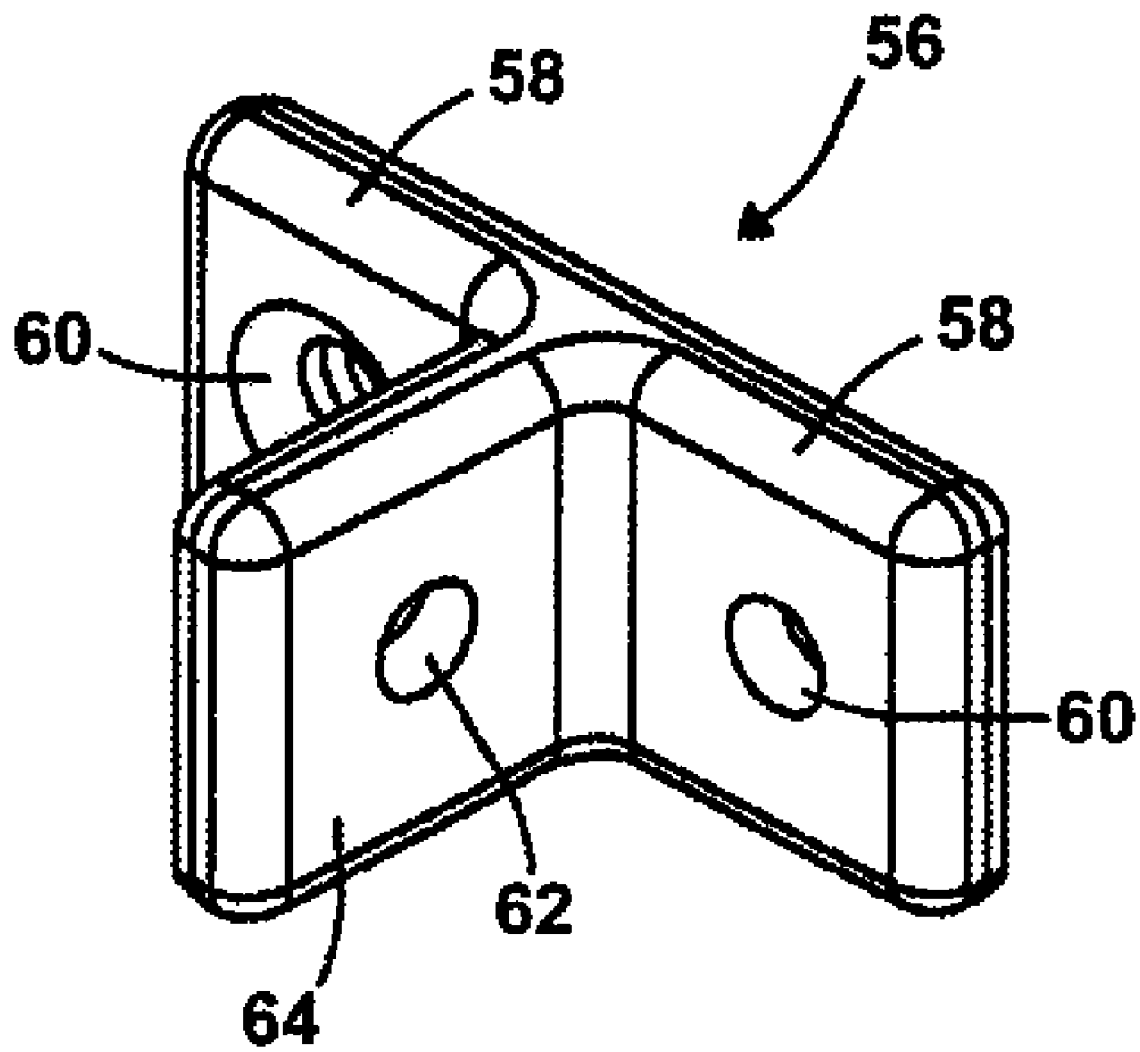
FIG. 7 illustrates the embodiment of FIG. 6 inserted with a facet implant spacer.

In another embodiment of the present invention, the screw 22 may be utilized with a facet implant 56. Facet implant 56, which can also be referred to as a spacer, is described in co-pending U.S. patent application Ser. No. 11/221,938, incorporated herein by reference in its entirety. As illustrated in FIG. 7, the facet implant 56 may include an articulating surface 56A. The facet implant 56 may be inserted and affixed such that the articulating surface rests between the opposing facet surfaces 24 and 26 to provide spacing and support between the facet surfaces 24 and 26. In one embodiment, one or more fixation tabs 58 may form a T-shape with an articulating surface 64 to secure the facet implant 56 in place, as shown in FIG. 7A. The fixation tabs 58 may be affixed to the vertebrae through holes 60, for example, by a bone fixation member, such as a pedicle screw, post, or adhesive. The facet implant 56 may be inserted before or after the screw 22 is inserted and the facet implant 56 may include a hole 62 to receive the screw. When the screw 22 is inserted first, the facet implant 56 requires some channel therein to fit around the intermediate portion 32a in order to properly place the implant 56. The facet implant 56 may help to provide more cushion and support to the facet joint and to spread out the strain of cushioning the facet joint over a wider surface. In addition, in alternative embodiments (for example, see FIG. 7A) the facet implant 56 may include one or more fixation wings 58 to help secure the facet implant 56 into the facet joint.

In yet another embodiment of the present invention, when the screw 22 or cord 52 is inserted between the opposing pair of facet surfaces 24 and 26 and into the lamina 27 and/or spinous process, the area may also be treated with bone growth promoting material. Alternatively, the proximal element 30 and distal element 28 of screw 22 may be coated with bone growth inducing material in order to decrease the time necessary for the opposing facet surfaces 24 and 26 to return to full strength after the procedure.

Various modifications and additions may be made to the exemplary structures and steps discussed. Various combinations, permutations, and rearrangements of those structures and steps may similarly be made without departing from the scope of the present invention. Accordingly, the scope of the present invention is intended to embrace all such alternatives, modifications, and variations as fall within the scope of the claims, together with all equivalents thereof.

The invention claimed is:

1. A system for stabilizing an opposing pair of facet surfaces, comprising:
   a facet implant for insertion between an opposing pair of facet surfaces, the facet implant including a hole, an articulating surface configured to rest between the opposing pair of facet surfaces and at least one fixation tab extending from the articulating surface, the at least one fixation tab configured to secure the facet implant in place between the opposing pair of facet surfaces, the facet implant providing spacing and support to the opposing facet surfaces;
   a cord for insertion through the opposing pair of facet surfaces, the cord inserted through the hole in the facet implant; and
   at least one bone anchor for anchoring the cord to the spine.

2. The system of claim 1 wherein the bone anchor is a pedicle screw.

3. A system for stabilizing the spine, comprising:
   a first facet implant having a first portion including an articulating surface and a second portion extending perpendicularly from the first portion forming substantially a T-shape, the first portion configured to be disposed between an opposing pair of facet surfaces and the second portion forming at least one fixation wing, the articulating surface configured to provide spacing and support to the opposing pair of facet surfaces, the at least one fixation wing configured to anchor the first facet implant to the spine; and
   a second implant configured to be inserted through the opposing pair of facet surfaces and through the first facet implant, the second facet implant including a screw with a distal end, a proximal end, and an intermediate portion, the intermediate portion flexibly linking the distal and proximal ends.

4. The system of claim 3, wherein the intermediate portion of the second implant comprises at least one of a spring, a cord, a polyaxial joint, a deformable metal, a deformable plastic, a ball and socket joint, and a U-joint.

5. The system of claim 3, wherein the intermediate portion of the second implant includes a ball and socket joint.

6. The system of claim 3, wherein the intermediate portion of the second implant includes a double ball configuration having a first ball and a second ball.

7. The system of claim 6, wherein the second implant includes a proximal element and a distal element articulatable relative to the proximal element, wherein the first ball fits into a cavity of the distal element, and the second ball fits into a cavity of the proximal element.

8. The system of claim 3, wherein the second implant includes a proximal element and a distal element, wherein the proximal element includes an engaging geometry complementary to an engaging geometry of the distal element;
   wherein when the proximal element is rotated in a first direction, the engaging geometry of the proximal element engages the engaging geometry of the distal element; and
   wherein when the proximal element is rotated in a second direction opposite the first direction, the engaging geometry of the proximal element disengages from the engaging geometry of the distal element.

9. The system of claim 8, wherein the engaging geometry of the proximal element includes an abutment surface, and the engaging geometry of the distal element includes an abutment surface configured to abut with the abutment surface of the proximal element.

* * * * *